(12) United States Patent
Zhou et al.

(10) Patent No.: US 9,565,413 B2
(45) Date of Patent: Feb. 7, 2017

(54) PICTURE INTERACTION METHOD, APPARATUS, SYSTEM AND MOBILE TERMINAL

(71) Applicant: TENCENT TECHNOLOGY (SHENZHEN) COMPANY LIMITED, Shenzhen (CN)

(72) Inventors: Bin Zhou, Shenzhen (CN); Mingliang Wang, Shenzhen (CN)

(73) Assignee: Tencent Technology (Shenzhen) Company Limited, Shenzhen (CN)

( * ) Notice: Subject to any disclaimer, the term of this patent is extended or adjusted under 35 U.S.C. 154(b) by 0 days.

(21) Appl. No.: 14/646,633

(22) PCT Filed: Sep. 22, 2013

(86) PCT No.: PCT/CN2013/083917
§ 371 (c)(1),
(2) Date: May 21, 2015

(87) PCT Pub. No.: WO2014/079269
PCT Pub. Date: May 30, 2014

(65) Prior Publication Data
US 2015/0296196 A1 Oct. 15, 2015

(30) Foreign Application Priority Data
Nov. 22, 2012 (CN) .......................... 2012 1 0478609

(51) Int. Cl.
*H04N 9/87* (2006.01)
*A61B 5/00* (2006.01)
(Continued)

(52) U.S. Cl.
CPC .............. *H04N 9/87* (2013.01); *A61B 5/0077* (2013.01); *A61B 5/024* (2013.01); *G06F 3/011* (2013.01);
(Continued)

(58) Field of Classification Search
CPC .............. A61B 2562/12; A61B 5/0077; H04N 21/422201
See application file for complete search history.

(56) References Cited

U.S. PATENT DOCUMENTS

2003/0158692 A1 8/2003 Tamada
2008/0262328 A1* 10/2008 Adams ............... A61B 5/14552
600/344
2010/0328088 A1 12/2010 Lin et al.

FOREIGN PATENT DOCUMENTS

CN 1397904 A 2/2003
CN 201299557 Y 9/2009
(Continued)

OTHER PUBLICATIONS

International Search Report for PCT/CN2013/083917, ISA/CN, mailed Jan. 2, 2014.

*Primary Examiner* — Huy T Nguyen
(74) *Attorney, Agent, or Firm* — Harness, Dickey & Pierce, P.L.C.

(57) ABSTRACT

Disclosed is a picture interaction method, which includes: setting a corresponding relation between a picture material moving speed and a user heartbeat frequency; presenting a picture material; shooting a user body image group, analyzing the user body image group so as to monitor a blood color difference, and calculating a user heartbeat frequency according to the blood color difference; and determining a picture material moving speed corresponding to the user heartbeat frequency according to the calculated user heartbeat frequency, and controlling moving of the picture material based on the determined picture material moving speed.

16 Claims, 5 Drawing Sheets

(51) Int. Cl.
*A61B 5/024* (2006.01)
*G06F 3/01* (2006.01)
*G11B 27/00* (2006.01)
*H04N 21/422* (2011.01)
*H04N 21/4223* (2011.01)
*H04N 21/472* (2011.01)
*H04N 21/431* (2011.01)
*H04N 21/442* (2011.01)

(52) U.S. Cl.
CPC ......... *G11B 27/005* (2013.01); *H04N 21/4223* (2013.01); *H04N 21/42201* (2013.01); *H04N 21/4318* (2013.01); *H04N 21/44218* (2013.01); *H04N 21/47217* (2013.01); *G06F 2203/011* (2013.01)

(56) References Cited

FOREIGN PATENT DOCUMENTS

| | | |
|---|---|---|
| CN | 201418109 Y | 3/2010 |
| CN | 102488508 A | 6/2012 |
| CN | 102525442 A | 7/2012 |

\* cited by examiner

PICTURE INTERACTION METHOD, APPARATUS, SYSTEM AND MOBILE TERMINAL

RELATED APPLICATION

This application claims priority to Chinese Patent Application No. 201210478609.0, filed with the Chinese Patent Office on Nov. 22, 2012 and entitled "PICTURE INTERACTION METHOD, APPARATUS, SYSTEM AND MOBILE TERMINAL", which is incorporated herein by reference in its entirety.

FIELD OF THE TECHNOLOGY

Implementation manners of this application relate to the field of information processing technologies, and in particular, to a picture interaction method, apparatus, system and a mobile terminal.

BACKGROUND OF THE DISCLOSURE

With rapid development of computer technologies and network technologies, the Internet and instant messaging technologies play an increasingly more important role in daily life, study and work of people. Besides, with development of the mobile Internet, the Internet is also developing towards mobility.

Today's society has entered a highly developed information age, an enterprise competition form has also transformed from a past single competition form that mainly focuses on product functions and quality into a compound competition form that uses an enterprise image, a product, a brand, and the like as important means and main tendency. The form transformation is inseparable from rapid development of modern picture presenting industry.

In conventional picture presenting activities, basic elements such as group of picture, picture content, a picture content audience, and picture representation reflect civilization degrees of ages in a certain area. All of these image elements serving as a type of culture reflect society and economy traces of ages to varying degrees.

In a current picture presenting method, normally, a picture material is provided by a picture supplier directly, and pictures are presented actively on a network in a unidirectional mode. However, this presenting manner does not take a personal participating degree of a picture audience into consideration, and is therefore just a type of partial picture presenting; this displaying manner lacks effective interaction with a picture browsing audience, so that an interaction success rate is low.

SUMMARY

An implementation manner of this application provides a picture interaction method, so as to improve an interaction success rate.

An implementation manner of this application further provides a picture interaction apparatus, so as to improve an interaction success rate.

An implementation manner of this application further provides a mobile terminal, so as to improve an interaction success rate.

An implementation manner of this application further provides a picture interaction system, so as to improve an interaction success rate.

Specific solutions of the implementation manners of this application are as follows:

A picture interaction method is provided, including: setting a corresponding relation between a picture material moving speed and a user heartbeat frequency, and further including:

presenting a picture material;

shooting a user body image group, analyzing the user body image group so as to monitor a blood color difference, and calculating a user heartbeat frequency according to the blood color difference; and determining a picture material moving speed corresponding to the user heartbeat frequency according to the calculated user heartbeat frequency, and controlling moving of the picture material based on the determined picture material moving speed.

A picture interaction apparatus is provided, including: a memory and a processor communicating with the memory, the memory being configured to store instructions that can be executed by the processor, and the instructions including a corresponding relation setting instruction, a picture material presenting instruction, a heartbeat frequency calculating instruction and a picture material moving instruction;

the corresponding relation setting instruction being used for instructing setting a corresponding relation between a picture material moving speed and a user heartbeat frequency;

the picture material presenting instruction being used for instructing presenting a picture material;

the heartbeat frequency calculating instruction being used for instructing shooting a user body image group, analyzing the user body image group so as to monitor a blood color difference, and calculating a user heartbeat frequency according to the blood color difference; and the picture material moving instruction being used for instructing determining a picture material moving speed corresponding to the user heartbeat frequency according to the calculated user heartbeat frequency, and controlling moving of the picture material based on the determined picture material moving speed.

A mobile terminal is provided, including: a memory and a processor communicating with the memory, the memory being configured to store instructions that can be executed by the processor, and the instructions including a displaying instruction, a shooting instruction and a calculating instruction;

the displaying instruction being used for instructing presenting a picture material;

the shooting instruction being used for instructing shooting a user body image group; and the calculating instruction being used for instructing storing a corresponding relation between a picture material moving speed and a user heartbeat frequency, analyzing the user body image group provided according to the shooting instruction so as to monitor a blood color difference, and calculating a user heartbeat frequency according to the blood color difference; and determining a picture material moving speed corresponding to the user heartbeat frequency according to the calculated user heartbeat frequency, and controlling moving of the picture material displayed according to the displaying instruction based on the determined picture material moving speed.

A picture interaction system is provided, including: a mobile terminal and a server;

the server being configured to receive a picture material, and send the picture material to the mobile terminal; and the mobile terminal including a memory and a processor communicating with the memory, the memory being configured to store one or more instructions that can be executed by the processor; when the one or more instructions are executed by the processor, the one or more instructions being used for instructing setting a corresponding relation between a picture material moving speed and a user heartbeat frequency; presenting the picture material received from the server; shooting a user body image group, analyzing the user body image group so as to monitor a blood color difference, and calculating a user heartbeat frequency according to the blood color difference; and determining a picture material moving speed corresponding to the user heartbeat frequency according to the calculated user heartbeat frequency, and controlling moving of the picture material based on the determined picture material moving speed.

It can be seen from the foregoing technical solutions that in the implementation manners of this application, a corresponding relation between a picture material moving speed and a user heartbeat frequency is set; a picture material is presented; a user body image group is shot, the user body image group is analyzed so as to monitor a blood color difference, and a user heartbeat frequency is calculated according to the blood color difference; and a picture material moving speed corresponding to the user heartbeat frequency is determined according to the calculated user heartbeat frequency, and moving of the picture material is controlled based on the determined picture material moving speed. It can be seen from this description that, after the implementation manners of this application are applied, a picture material supplier (such as an advertiser) no longer provides a picture material in a unidirectional mode, but instead a user can control moving of the picture material based on a heartbeat frequency, and therefore the implementation manners of this application improve an interaction success rate of the picture material effectively.

Besides, in the implementation manners of this application, a picture material is controlled by sensing a user heartbeat, and an exposure degree of the picture material is further improved, and therefore a launching effect of the picture material can be further improved.

DESCRIPTION OF EMBODIMENTS

To make technical solutions and advantages of this application clearer, this application is further described in detail below with reference to the accompanying drawings.

Figure 1:
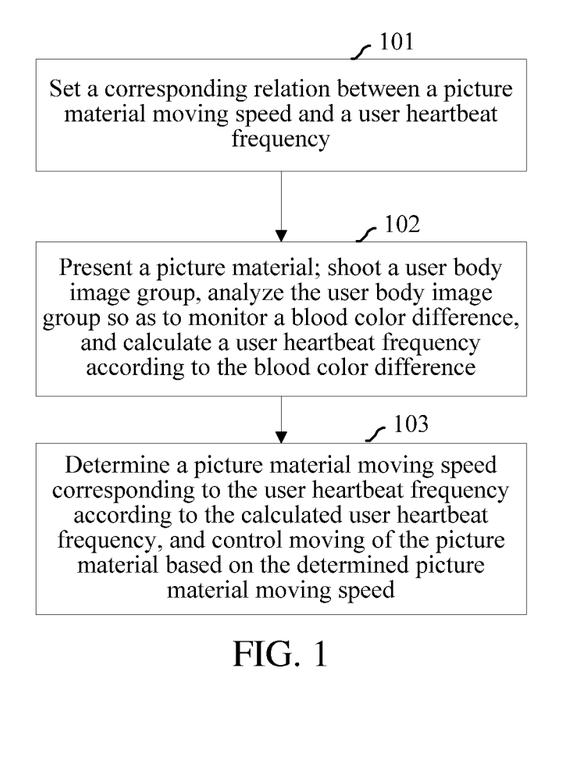
FIG. 1 is a flowchart of a picture interaction method according to an implementation manner of this application.

FIG. 1 is a flowchart of a picture interaction method according to an implementation manner of this application.

As shown in FIG. 1, the method includes:

Step 101: Set a corresponding relation between a picture material moving speed and a user heartbeat frequency.

Here, the corresponding relation between a picture material moving speed and a user heartbeat frequency is preferably set to an ascending relation. Therefore, when a quicker user heartbeat frequency is sensed, a subsequent controlled picture material moving speed is quicker.

Optionally, the corresponding relation between a picture material moving speed and a user heartbeat frequency may further be set to a descending relation. Therefore, when a slower user heartbeat frequency is sensed, a subsequent controlled picture material moving speed is quicker.

In one implementation manner, the corresponding relation between a picture material moving speed and a user heartbeat frequency can be stored in a mobile terminal. The mobile terminal may include but is not limited to: a feature phone, a smartphone, a palm computer, a personal computer (PC), a tablet computer or a personal digital assistant (PDA).

Although specific examples of the mobile terminal are listed in detail above, a person skilled in the art can realize that the listed examples are merely for purpose of description, but are not intended to limit the protection scope of the implementation manner of this application. The mobile terminal can be applied to any intelligent terminal operating system, and specifically, an operating system that can be used includes but is not limited to: Android, Palm OS, Symbian, Windows mobile, Linux, iPhone (Apple) OS, Black Berry OS 6.0, Windows Phone series, and the like.

Preferably, the mobile terminal specifically can use an Android operating system, and the mobile terminal can use each version of Android, which includes but is not limited to: Astro (Android Beta), Bender (Android 1.0), Cupcake (Android 1.5), Donut (Android 1.6), Éclair (Android 2.0/2.1), Froyo (Android 2.2), Gingerbread (Android 2.3), Honeycomb (Android 3.0), Ice Cream Sandwich (Android 4.0), Jelly Bean (Android 4.1), and the like. Specific versions of an Android platform are listed in detail above; a person skilled in the art can realize that the implementation manner of this application is not limited to the foregoing listed versions, and the implementation manner of this application can further be applied to any other version based on an Android software architecture.

Step 102: Present a picture material; shoot a user body image group, analyze the user body image group so as to monitor a blood color difference, and calculate a user heartbeat frequency according to the blood color difference.

Here, an image audience, an image supplier or any third party can upload a picture material to a server located at a network side in various information transmitting manners, and then the mobile terminal obtains the picture material from the server, and presents the picture material.

Specific content of the picture material relates to the material itself that is expected to be presented to a user. For example, assuming that an information push about a branded automobile is expected to be launched, a physical model image of the branded automobile can be uploaded; and assuming that an information push about an electronic product is expected to be launched, a physical module image of the electronic product can be uploaded.

A background image corresponding to the picture material can further be presented on the mobile terminal. There are many types of background images and picture materials. For example, the background image and the picture material may respectively be: a bitmap, a joint photographic experts group (JPEG), a tagged image file format (TIFF), a graphics interchange format (GIF), a portable network graphic format (PNG), or a three-dimensional image. Data of a GIF image file is compressed, and uses a compression algorithm such as a variable length compression algorithm. Another feature of the GIF format is that multiple color images can be stored in a GIF file, and if data of multiple images stored in a file is read and displayed on a screen one by one, a simplest picture can be constructed.

In the implementation manner of this application, collective displaying can be implemented by superimposing a picture material of this picture type onto a background image.

Figure 2:
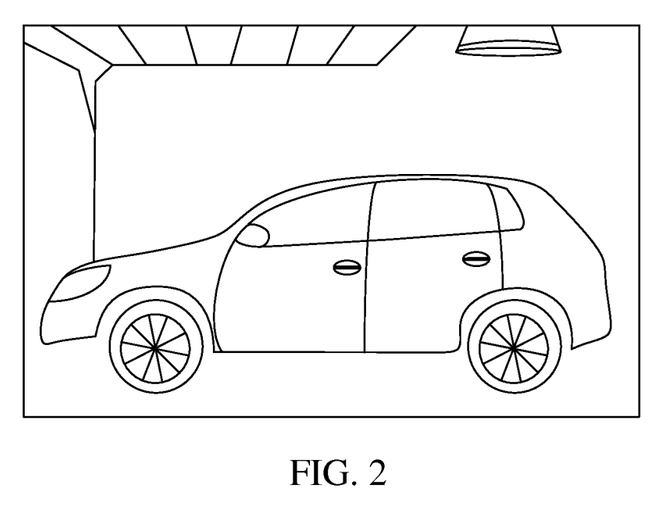
FIG. 2 is a schematic diagram of a picture material of an automobile type according to an implementation manner of this application.

Exemplarily, FIG. 2 is a schematic diagram of a picture material of an automobile type according to an implementation manner of this application. It can be seen from FIG. 2 that, the picture material is an automobile model, and a background image is a house. The automobile model and the house are merged and presented together, and the automobile model stops inside the house.

Besides, an information push audience, an image supplier or any third party can upload a picture material in multiple manners. For example, the picture material can be uploaded by an image audience in a wireless network access manner on a mobile terminal directly; and the picture material can also be uploaded by the image supplier to a server by means of a personal computer (PC) or the like.

Preferably, the mobile terminal can obtain the background image and the picture material from the server by means of a common gateway interface (CGI), and the background image and the picture material are displayed on a browser window of the mobile terminal.

A mobile terminal browser is a browser that runs on the mobile terminal, and can browse Internet content online in multiple manners such as general packet radio service (GPRS). Currently, some mobile terminal browsers need to be supported by a JAVA system or a mobile terminal system (such as an Apple IOS system and an Android platform).

The server can provide the background image to the mobile terminal, and can also store the background image in the mobile terminal locally in advance. The background image is preferably stored in the server, which is because the server can have bigger storage space relative to that of the mobile terminal. Therefore, a massive quantity of background images can be stored in the server. Exemplarily, the background image may include: a blue sky, white cloud, a bridge, a highway, and the like.

In an implementation manner, besides uploading the picture material, the image audience, the image supplier or any third party can further upload image attribute information for describing the type of the picture material. The image attribute information may be text information. The type of the picture material may further be described directly by using a name of the picture material. The server can determine the type of the picture material according to the image attribute information, and retrieve a background image matching the picture material.

For example, assuming that the picture material is an information push about a car, the server can retrieve a background image suitable for the automobile (such as a runway); and assuming that the picture material is an information push about an electronic product, the server can retrieve a background image suitable for the electronic product (such as a desk).

Here, when the background image is provided by the server, the server can first send the uploaded picture material and the background image stored in the server to the mobile terminal, and preferably send order information and/or advertisement position information incidentally, which are provided to the mobile terminal for corresponding presenting.

The background image and the picture material are displayed together on the mobile terminal, thereby merging and displaying the background image and the picture material. Preferably, the picture material is displayed on or in front of the background image.

After the picture material is presented to a user, an interaction process of the picture material can be implemented based on a user heartbeat frequency. Every heart impulse of the user pumps oxygenated blood to organs of the body, and the color of the oxygenated blood differs from that of deoxygenated blood. Therefore, inspection of the heart frequency can be implemented by inspecting a color difference between the oxygenated blood and the deoxygenated blood. Preferably, because a blood flowing speed of a fingertip and that of a tiptoe are relatively slow, which helps distinguish color differences, the user heartbeat frequency is generally calculated using a fingertip image or a tiptoe image.

After the user approaches or attaches a camera of the mobile terminal by using a finger or toe, the camera and an LED flash light are triggered to start up; and under strong light, a periodical effect on reflected light occurring when the blood flows through the finger or the toe is sensed by the camera, so as to calculate the heartbeat frequency.

Specifically, the camera first captures a group of finger images or toe images; and then an image area of a center area is extracted from each of the finger images or toe images and converted into a gray scale image, and then a gray scale median of each of the gray scale images is obtained. After a certain quantity of gray scale images are collected, a group of gray scale medians are obtained; a minimum value and a maximum value are obtained from data of the group of gray scale medians; statistics on an occurrence frequency of the maximum value is collected according to time, and the minimum value is used for verification, so as to calculate the heartbeat frequency.

In an implementation manner, the user body image group is a user finger image group or a user toe image group. In this case, first, a predetermined quantity of user body images are extracted from the user body image group, and center area images are captured from the user body images; then, the center area images are converted into gray scale images, a gray scale median of each of the gray scale images is calculated, and the user heartbeat frequency is calculated according to an occurrence frequency of a peak value of gray scale medians.

In another implementation manner, the user body image group is a user finger image group or a user toe image group. In this case, first, a predetermined quantity of user body images are extracted from the user body image group, and center area images are captured from the user body images; the center area images are converted into gray scale images, a gray scale median of each of the gray scale images is calculated, and the user heartbeat frequency is calculated according to an occurrence frequency of a valley value of gray scale medians.

Preferably, the user body image group is a user finger image group or a user toe image group. In this case, first, a predetermined quantity of user body images are extracted from the user body image group, and center area images are captured from the user body images; the center area images are converted into gray scale images, a gray scale median of each of the gray scale images is calculated, the user heartbeat frequency is calculated according to an occurrence frequency of a peak value of gray scale medians, and the calculated user heartbeat frequency is further verified according to an occurrence frequency of a valley value of gray scale medians.

Step 103: Determine a picture material moving speed corresponding to the user heartbeat frequency according to the calculated user heartbeat frequency, and control moving of the picture material based on the determined picture material moving speed.

Here, when the relation between a picture material moving speed and a user heartbeat frequency is set to an ascending relation, if the heartbeat frequency is quicker, the picture material moving speed is quicker; and when the relation between a picture material moving speed and a user heartbeat frequency is set to a descending relation, if the heartbeat frequency is quicker, the picture material moving speed is slower.

A user heartbeat frequency level interval can be further set in advance, and a corresponding relation between a picture material moving speed and a user heartbeat frequency level interval is set. Afterwards, a user heartbeat frequency level interval in which the calculated user heartbeat frequency is located is first determined, and a picture material moving speed corresponding to the user heartbeat frequency level interval is determined; and then moving of the picture material is controlled based on the determined picture material moving speed.

For example, after the camera senses the heartbeat frequency, values of the heartbeat frequency can be classified into one of level types such as a quick type, a normal type, and a slow type, and finally a corresponding value is reflected on a rotating effect of the picture material.

Preferably, after a finger of a viewer leaves the camera, the picture material rapidly moves out of a visible displaying range at a last obtained speed.

Figure 3:
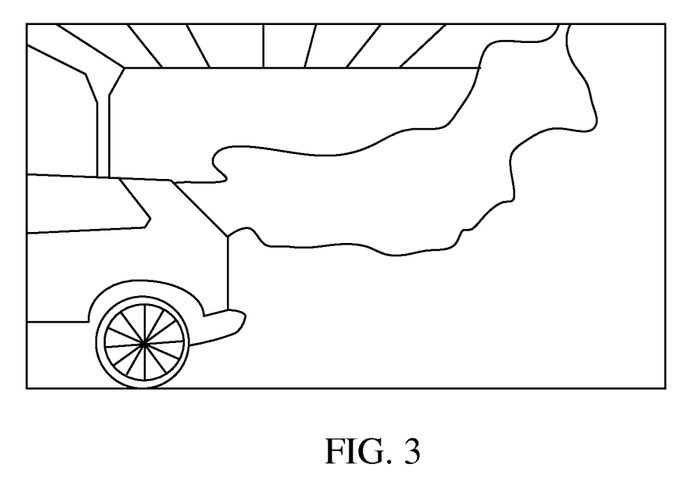
FIG. 3 is a schematic diagram of interaction and moving of a picture material of an automobile type according to an implementation manner of this application.

FIG. 3 is a schematic diagram of interaction and moving of a picture material of an automobile type according to an implementation manner of this application.

It can be seen from FIG. 3 that, the picture material is an automobile model, and a background image is a house. The automobile model and the house are merged and presented together, and the automobile model stops on the house. After a user heartbeat frequency is sensed, the automobile model can be moved away from the house according to a moving speed corresponding to the heartbeat frequency. Besides, when a user puts a finger or a toe near a camera, heat of the user can be sensed by a heat sensor of the camera, and a preset engine start-up sound starts to be played, so as to indicate that the automobile model starts up.

Based on the foregoing specific analysis, an implementation manner of this application further provides a picture interaction apparatus.

Figure 4:
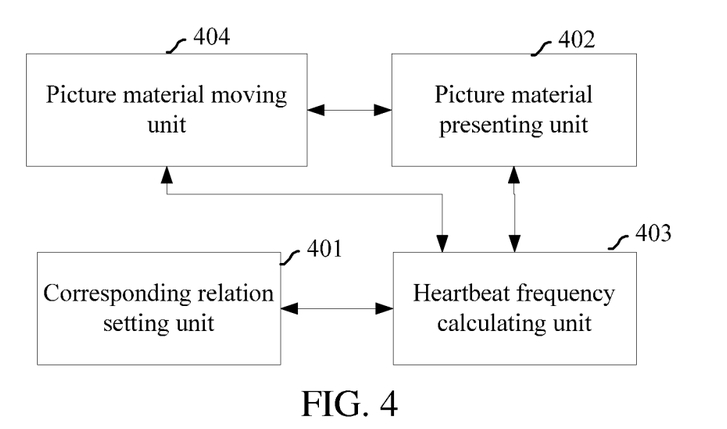
FIG. 4 is a structural diagram of a picture interaction apparatus according to an implementation manner of this application.

FIG. 4 is a structural diagram of a picture interaction apparatus according to an implementation manner of this application.

As shown in FIG. 4, the apparatus includes a corresponding relation setting unit 401, a picture material presenting unit 402, a heartbeat frequency calculating unit 403 and a picture material moving unit 404, where the corresponding relation setting unit 401 is configured to set a corresponding relation between a picture material moving speed and a user heartbeat frequency;

the picture material presenting unit 402 is configured to present a picture material;

the heartbeat frequency calculating unit 403 is configured to shoot a user body image group, analyze the user body image group so as to monitor a blood color difference, and calculate a user heartbeat frequency according to the blood color difference; and the picture material moving unit 404 is configured to determine a picture material moving speed corresponding to the user heartbeat frequency according to the calculated user heartbeat frequency, and control moving of the picture material based on the determined picture material moving speed.

In an implementation manner, the user body image group is a user finger image group or a user toe image group; and the heartbeat frequency calculating unit 403 is configured to extract a predetermined quantity of user body images from the user body image group, and capture center area images from the user body images; and convert the center area images into gray scale images, calculate a gray scale median of each of the gray scale images, and calculate the user heartbeat frequency according to an occurrence frequency of a peak value of gray scale medians.

In an implementation manner, the user body image group is a user finger image group or a user toe image group; and the heartbeat frequency calculating unit 403 is configured to extract a predetermined quantity of user body images from the user body image group, and capture center area images from the user body images; and convert the center area images into gray scale images, calculate a gray scale median of each of the gray scale images, and calculate the user heartbeat frequency according to an occurrence frequency of a valley value of gray scale medians.

In an implementation manner, the user body image group is a user finger image group or a user toe image group; and the heartbeat frequency calculating unit 403 is configured to extract a predetermined quantity of user body images from the user body image group, and capture center area images from the user body images; and convert the center area images into gray scale images, calculate a gray scale median of each of the gray scale images, calculate the user heartbeat frequency according to an occurrence frequency of a peak value of gray scale medians, and further verify the calculated user heartbeat frequency according to an occurrence frequency of a valley value of gray scale medians.

Preferably, the corresponding relation setting unit 401 is configured to set the corresponding relation between a picture material moving speed and a user heartbeat frequency to an ascending relation.

Preferably, the corresponding relation setting unit 401 is configured to set a user heartbeat frequency level interval, and set a corresponding relation between a picture material moving speed and a user heartbeat frequency level interval; and the picture material moving unit 402 is configured to determine a user heartbeat frequency level interval in which the user heartbeat frequency is located, and determine a picture material moving speed corresponding to the user heartbeat frequency level interval; and control moving of the picture material based on the determined picture material moving speed.

Implementation manners of this application can be implemented in multiple application environments based on the foregoing method and apparatus. For example, the implementation manners of this application can be applied to an advertisement application of a mobile terminal. After a user clicks on an advertisement, a camera and an LED flash light of the mobile terminal are triggered to start up. Under strong light of the LED flash light, a periodical effect on reflected light occurring when blood flows through a fingertip is sensed by the camera of the mobile terminal, so as to calculate a heartbeat frequency and control an object in the advertisement, which therefore further improves interactivity and novelty of the advertisement.

For example, after a mobile terminal logs on to a microblog or mobile instant messaging software starts up, a start-up picture advertisement is played first, and an object (such as an automobile) is in the advertisement. After a user catches sight of the advertisement, the user clicks on words in the advertisement and can put a finger onto a camera of the mobile terminal according to a word prompt in the advertisement. Afterwards, a user heartbeat speed can be quickly calculated by applying the implementation manners of this application, so as to start up the automobile in the advertisement, thereby implementing interaction between the user heartbeat and the advertisement.

Based on the foregoing analysis, an implementation manner of this application further provides a mobile terminal.

Figure 5:
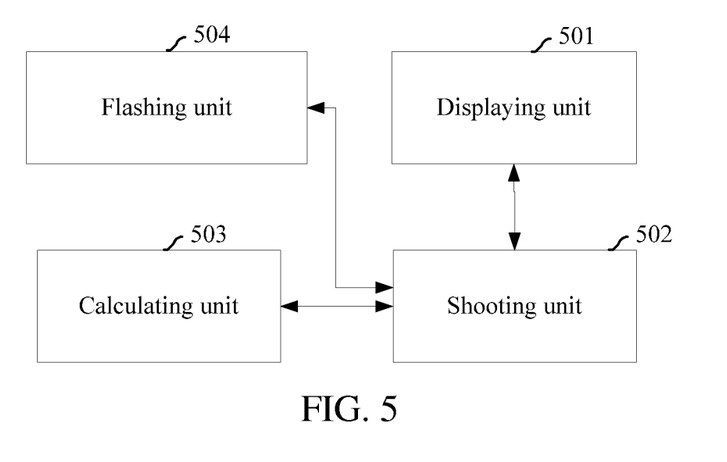
FIG. 5 is a schematic structural diagram of a mobile terminal according to an implementation manner of this application.

FIG. 5 is a schematic structural diagram of a mobile terminal according to an implementation manner of this application.

As shown in FIG. 5, the mobile terminal includes a displaying unit 501, a shooting unit 502 and a calculating unit 503, where the displaying unit 501 is configured to present a picture material;

the shooting unit 502 is configured to shoot a user body image group; and the calculating unit 503 is configured to store a corresponding relation between a picture material moving speed and a user heartbeat frequency, analyze the user body image group provided by the shooting unit 502 so as to monitor a blood color difference, and calculate a user heartbeat frequency according to the blood color difference; and determine a picture material moving speed corresponding to the user heartbeat frequency according to the calculated user heartbeat frequency, and control moving of the picture material in the displaying unit based on the determined picture material moving speed.

Preferably, the mobile terminal further includes a flashing unit 504. The flashing unit 504 is configured to provide a flash light source when the user body image group is shot by the shooting unit.

In an implementation manner, the calculating unit 503 is configured to set a user heartbeat frequency level interval and a corresponding relation between a picture material moving speed and a user heartbeat frequency level interval, determine a user heartbeat frequency level interval in which the user heartbeat frequency is located, and determine a picture material moving speed corresponding to the user heartbeat frequency level interval; and control moving of the picture material based on the determined picture material moving speed.

Preferably, the shooting unit 502 is further configured to sense heat of a user, and send a heat prompt message to the displaying unit 501 after sensing the heat of the user; and the displaying unit 501 is further configured to play start-up audio of moving the picture material after receiving the heat prompt message.

Based on the foregoing specific analysis, an implementation manner of this application further provides a picture interaction system.

Figure 6:
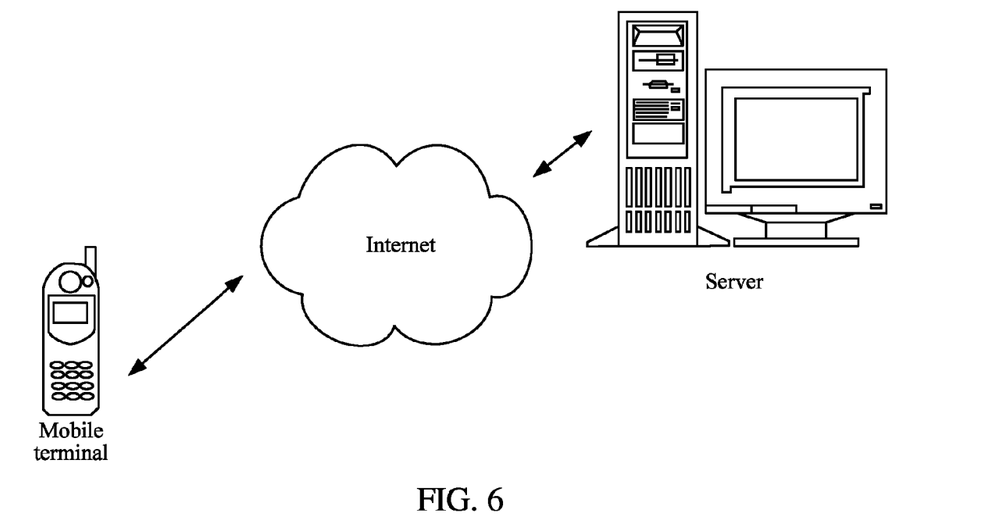
FIG. 6 is a structural diagram of a picture interaction system according to an implementation manner of this application.

FIG. 6 is a structural diagram of a picture interaction system according to an implementation manner of this application.

As shown in FIG. 6, the system includes a mobile terminal 601 and a server 602, where the server 602 is configured to receive a picture material, and send the picture material to the mobile terminal 601; and the mobile terminal 601 is configured to set a corresponding relation between a picture material moving speed and a user heartbeat frequency; present a picture material received from the server 602; shoot a user body image group, analyze the user body image group so as to monitor a blood color difference, and calculate a user heartbeat frequency according to the blood color difference; and determine a picture material moving speed corresponding to the user heartbeat frequency according to the calculated user heartbeat frequency, and control moving of the picture material based on the determined picture material moving speed.

The mobile terminal 601 may include but is not limited to: a feature phone, a smartphone, a palm computer, a personal computer (PC), a tablet computer or a personal digital assistant (PDA).

Besides, here, an image audience, an image supplier or any third party can upload a picture material to the server 602 located at a network side in various information transmitting manners, and then the mobile terminal 601 obtains the picture material from the server 602, and presents the picture material.

An embodiment of this application further provides a machine readable storage medium, which stores instructions used to enable a machine to execute the picture interaction method described herein. Specifically, a system or an apparatus equipped with the storage medium can be provided, where software program code for implementing functions of any embodiment of the foregoing embodiments is stored in the storage medium, and the program code stored in the storage medium is read and executed by a computer (or a CPU or an MPU) of the system or the apparatus.

In this case, the program code read from the storage medium can implement functions of any embodiment of the foregoing embodiments, and therefore the program code and the storage medium for storing the program code constitute a part of this application.

Figure 7:
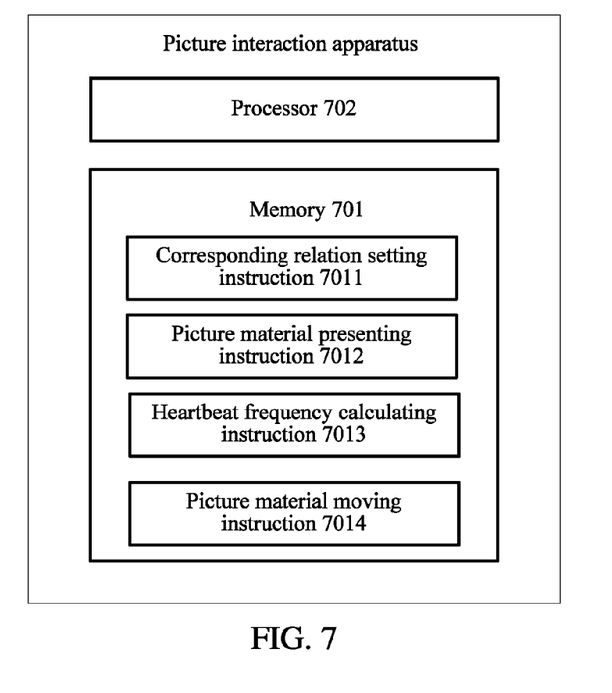
FIG. 7 is a structural diagram of another picture interaction apparatus according to an implementation manner of this application.

For example, FIG. 7 is a structural diagram of another picture interaction apparatus according to an implementation manner of this application.

As shown in FIG. 7, the apparatus includes a memory 701 and a processor 702 communicating with the memory 701, where the memory 701 stores a corresponding relation setting instruction 7011, a picture material presenting instruction 7012, a heartbeat frequency calculating instruction 7013 and a picture material moving instruction 7014 that can be executed by the processor 702.

The corresponding relation setting instruction 7011 is used for instructing setting a corresponding relation between a picture material moving speed and a user heartbeat frequency.

The picture material presenting instruction 7012 is used for instructing presenting a picture material.

The heartbeat frequency calculating instruction 7013 is used for instructing shooting a user body image group, analyzing the user body image group so as to monitor a blood color difference, and calculating a user heartbeat frequency according to the blood color difference.

The picture material moving instruction 7014 is used for instructing determining a picture material moving speed corresponding to the user heartbeat frequency according to the calculated user heartbeat frequency, and controlling moving of the picture material based on the determined picture material moving speed.

Functions implemented by the corresponding relation setting instruction 7011, the heartbeat frequency calculating instruction 7013, and the picture material moving instruction 7014, when being executed by the processor 702 are the same as functions implemented by the corresponding relation setting unit 401, the heartbeat frequency calculating unit 403, and the picture material moving unit 404, in the example shown in FIG. 4, and are not further described herein.

Figure 8:
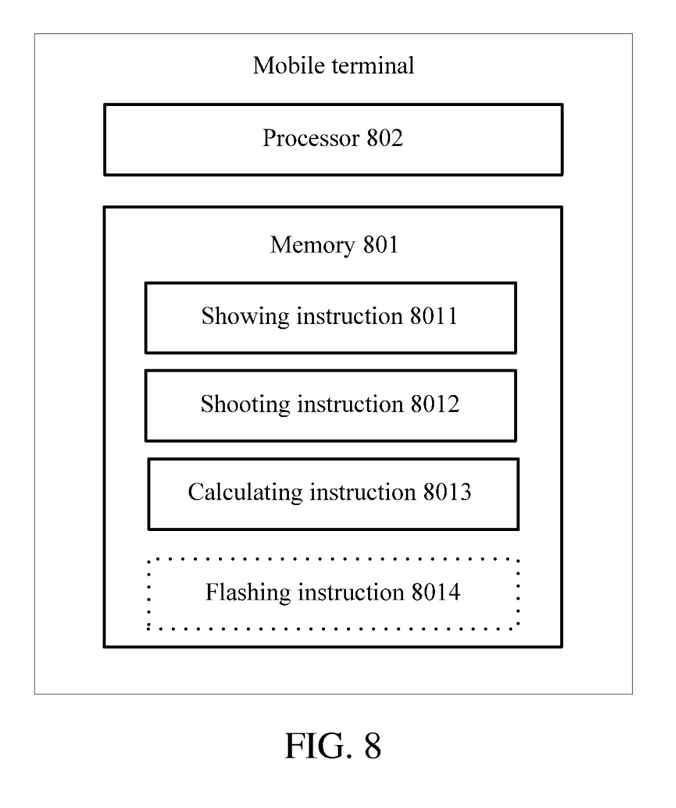
FIG. 8 is a schematic structural diagram of another mobile terminal according to an implementation manner of this application.

FIG. 8 is a schematic structural diagram of another mobile terminal according to an implementation manner of this application.

As shown in FIG. 8, the mobile terminal includes a memory 801 and a processor 802 communicating with the memory 801, where the memory 801 stores a displaying instruction 8011, a shooting instruction 8012 and a calculating instruction 8013 that can be executed by the processor 802.

The displaying instruction 8011 is used for instructing presenting a picture material;

the shooting instruction 8012 is used for instructing shooting a user body image group; and the calculating instruction 8013 is used for instructing storing a corresponding relation between a picture material moving speed and a user heartbeat frequency, analyzing the user body image group provided according to the shooting instruction 8012 so as to monitor a blood color difference, and calculating a user heartbeat frequency according to the blood color difference; and determining a picture material moving speed corresponding to the user heartbeat frequency according to the calculated user heartbeat frequency, and controlling moving of the picture material in a displaying unit based on the determined picture material moving speed.

The memory 801 further stores a flashing instruction 8014 that can be executed by the processor 802. The flashing instruction 8014 is used for instructing providing a flash light source when the user body image group is shot according to the shooting instruction 8012.

Functions implemented by the displaying instruction 8011, the shooting instruction 8012, and the calculating instruction 8013 when being executed by the processor 802 are the same as functions implemented by the displaying unit 501, the shooting unit 502, and the calculating unit 503 in the example shown in FIG. 5, and are not further described herein.

In conclusion, in the implementation manners of this application, a corresponding relation between a picture material moving speed and a user heartbeat frequency is set; a picture material is presented; a user body image group is shot, the user body image group is analyzed so as to monitor a blood color difference, and a user heartbeat frequency is calculated according to the blood color difference; and a picture material moving speed corresponding to the user heartbeat frequency is determined according to the calculated user heartbeat frequency, and moving of the picture material is controlled based on the determined picture material moving speed. It can be seen from this description that, after the implementation manners of this application are applied, a picture material supplier (such as an advertiser) no longer provides a picture material in a unidirectional mode, but instead a user can control a moving manner of the picture material based on a heartbeat frequency, and therefore the implementation manners of this application improve an interaction success rate of the picture material effectively.

Besides, in the implementation manners of this application, a picture material is controlled by sensing a user heartbeat, and an exposure degree of the picture material is improved, and therefore a launching effect of the picture material can be further improved.

The foregoing descriptions are merely preferred embodiments of this application, but are not intended to limit the protection scope of this application. Any modification, equivalent replacement, or improvement made within the spirit and principle of this application shall fall within the protection scope of this application.

What is claimed is:

1. A picture interaction method performed by a processor by executing instructions stored in a memory, comprising setting a corresponding relation between a picture material moving speed and a user heartbeat frequency, and further comprising:

presenting a picture material;

shooting a user body image group, analyzing the user body image group so as to monitor a blood color difference, and calculating a user heartbeat frequency according to the blood color difference; and determining a picture material moving speed corresponding to the user heartbeat frequency according to the calculated user heartbeat frequency, and controlling moving of the picture material based on the determined picture material moving speed.

2. The picture interaction method according to claim 1, wherein the user body image group is a user finger image group or a user toe image group;

the analyzing the user body image group so as to monitor a blood color difference, and calculating a user heartbeat frequency according to the blood color difference comprises:

extracting a predetermined quantity of user body images from the user body image group, and capturing center area images from the user body images; and converting the center area images into gray scale images, calculating a gray scale median of each of the gray scale images, and calculating the user heartbeat frequency according to an occurrence frequency of a peak value of gray scale medians.

3. The picture interaction method according to claim 1, wherein the user body image group is a user finger image group or a user toe image group;

the analyzing the user body image group so as to monitor a blood color difference, and calculating a user heartbeat frequency according to the blood color difference comprises:

extracting a predetermined quantity of user body images from the user body image group, and capturing center area images from the user body images; and converting the center area images into gray scale images, calculating a gray scale median of each of the gray scale images, and calculating the user heartbeat frequency according to an occurrence frequency of a valley value of gray scale medians.

4. The picture interaction method according to claim 1, wherein the user body image group is a user finger image group or a user toe image group;
  the analyzing the user body image group so as to monitor a blood color difference, and calculating a user heartbeat frequency according to the blood color difference comprises:
  extracting a predetermined quantity of user body images from the user body image group, and capturing center area images from the user body images; and
  converting the center area images into gray scale images, calculating a gray scale median of each of the gray scale images, calculating the user heartbeat frequency according to an occurrence frequency of a peak value of gray scale medians, and further verifying the calculated user heartbeat frequency according to an occurrence frequency of a valley value of gray scale medians.

5. The picture interaction method according to claim 1, wherein the setting a corresponding relation between a picture material moving speed and a user heartbeat frequency is: setting the relation between a picture material moving speed and a user heartbeat frequency to an ascending relation.

6. The picture interaction method according to claim 1, wherein the setting a corresponding relation between a picture material moving speed and a user heartbeat frequency is:
  setting a user heartbeat frequency level interval, and setting a corresponding relation between a picture material moving speed and a user heartbeat frequency level interval; and
  the determining a picture material moving speed corresponding to the user heartbeat frequency according to the calculated user heartbeat frequency, and controlling moving of the picture material based on the determined picture material moving speed comprises:
  determining a user heartbeat frequency level interval in which the user heartbeat frequency is located, and determining a picture material moving speed corresponding to the user heartbeat frequency level interval; and
  controlling moving of the picture material based on the determined picture material moving speed.

7. A picture interaction apparatus comprising a memory and a processor communicating with the memory, the memory being configured to store instructions that when executed by the processor configure the picture interaction apparatus to:
  set a corresponding relation between a picture material moving speed and a user heartbeat frequency;
  present a picture material;
  shoot a user body image group, analyze the user body image group so as to monitor a blood color difference, and calculate a user heartbeat frequency according to the blood color difference; and
  determine a picture material moving speed corresponding to the user heartbeat frequency according to the calculated user heartbeat frequency, and control moving of the picture material based on the determined picture material moving speed.

8. The picture interaction apparatus according to claim 7, wherein the user body image group is a user finger image group or a user toe image group; and
  wherein the picture interaction apparatus is further configured to extract a predetermined quantity of user body images from the user body image group, and capture center area images from the user body images; and to convert the center area images into gray scale images, calculate a gray scale median of each of the gray scale images, and calculate the user heartbeat frequency according to an occurrence frequency of a peak value of gray scale medians.

9. The picture interaction apparatus according to claim 7, wherein the user body image group is a user finger image group or a user toe image group; and
  wherein the picture interaction apparatus is further configured to extract a predetermined quantity of user body images from the user body image group, and capture center area images from the user body images; and to convert the center area images into gray scale images, calculate a gray scale median of each of the gray scale images, and calculate the user heartbeat frequency according to an occurrence frequency of a valley value of gray scale medians.

10. The picture interaction apparatus according to claim 7, wherein the user body image group is a user finger image group or a user toe image group; and
  wherein the picture interaction apparatus is further configured to extract a predetermined quantity of user body images from the user body image group, and capture center area images from the user body images; and to convert the center area images into gray scale images, calculate a gray scale median of each of the gray scale images, calculate the user heartbeat frequency according to an occurrence frequency of a peak value of gray scale medians, and further verify the calculated user heartbeat frequency according to an occurrence frequency of a valley value of gray scale medians.

11. The picture interaction apparatus according to claim 7, wherein the picture interaction apparatus is further configured to:
  set the relation between a picture material moving speed and a user heartbeat frequency to an ascending relation.

12. The picture interaction apparatus according to claim 7, wherein the picture interaction apparatus is further configured to:
  set a user heartbeat frequency level interval, and set a corresponding relation between a picture material moving speed and a user heartbeat frequency level interval; and
  determine a user heartbeat frequency level interval in which the user heartbeat frequency is located, and determine a picture material moving speed corresponding to the user heartbeat frequency level interval; and control moving of the picture material based on the determined picture material moving speed.

13. A mobile terminal comprising a memory and a processor communicating with the memory, the memory being configured to store instructions that when executed by the processor cause the mobile terminal to:
  present a picture material;
  shoot a user body image group; and
  store a corresponding relation between a picture material moving speed and a user heartbeat frequency, analyze the user body image group so as to monitor a blood color difference, and calculate a user heartbeat frequency according to the blood color difference; and
  determine a picture material moving speed corresponding to the user heartbeat frequency according to the calculated user heartbeat frequency, and control moving of the picture material based on the determined picture material moving speed.

14. The mobile terminal according to claim 13, wherein the mobile terminal is further configured to:
provide a flash light source when the user body image group is shot.

15. The mobile terminal according to claim 13, wherein the mobile terminal is further configured to:
set a user heartbeat frequency level interval and a corresponding relation between a picture material moving speed and a user heartbeat frequency level interval, determine a user heartbeat frequency level interval in which the user heartbeat frequency is located, and determine a picture material moving speed corresponding to the user heartbeat frequency level interval; and
control moving of the picture material based on the determined picture material moving speed.

16. The mobile terminal according to claim 13, wherein the mobile terminal is further configured to:
sense heat of a user, and sending a heat prompt message after the heat of the user is sensed; and
play start-up audio of moving the picture material after the heat prompt message is received.

* * * * *